US010745564B2

(12) United States Patent
Zhao et al.

(10) Patent No.: US 10,745,564 B2
(45) Date of Patent: Aug. 18, 2020

(54) DYE FOR DYEING COTTON FIBER IN SUPERCRITICAL CARBON DIOXIDE, PREPARATION METHOD AND APPLICATION THEREOF

(71) Applicant: DALIAN POLYTECHNIC UNIVERSITY, Dalian, Liaoning (CN)

(72) Inventors: Hongjuan Zhao, Liaoning (CN); Laijiu Zheng, Liaoning (CN); Huanda Zheng, Liaoning (CN); Jun Yan, Liaoning (CN); Xiaoqing Xiong, Liaoning (CN); Miao Liu, Liaoning (CN); Ju Wei, Liaoning (CN)

(73) Assignee: DALIAN POLYTECHNIC UNIVERSITY, Dalian, Liaoning (CN)

(*) Notice: Subject to any disclaimer, the term of this patent is extended or adjusted under 35 U.S.C. 154(b) by 0 days.

(21) Appl. No.: 16/342,160

(22) PCT Filed: Oct. 19, 2017

(86) PCT No.: PCT/CN2017/106813
§ 371 (c)(1),
(2) Date: Apr. 15, 2019

(87) PCT Pub. No.: WO2018/072723
PCT Pub. Date: Apr. 26, 2018

(65) Prior Publication Data
US 2019/0233650 A1 Aug. 1, 2019

(30) Foreign Application Priority Data
Oct. 20, 2016 (CN) .......................... 2016 1 0916304

(51) Int. Cl.
C09B 61/00 (2006.01)
D06P 1/94 (2006.01)
(Continued)

(52) U.S. Cl.
CPC ............ *C09B 61/00* (2013.01); *C09B 23/105* (2013.01); *D06P 1/00* (2013.01); *D06P 1/34* (2013.01);
(Continued)

(58) Field of Classification Search
CPC . C09B 67/0096; C09B 61/00; C09B 67/0097; C09B 23/105; D06P 1/34;
(Continued)

(56) References Cited

U.S. PATENT DOCUMENTS 7,749,286 B2 * 7/2010 Greaves .................. A61K 8/19
8/405

FOREIGN PATENT DOCUMENTS

CN 103408961 A 11/2013
CN 103952008 A 7/2014
(Continued)

OTHER PUBLICATIONS

STIC Search Report dated Jan. 27, 2020.*
(Continued)

Primary Examiner — Eisa B Elhilo
(74) Attorney, Agent, or Firm — Novick, Kim, & Lee, PLLC; Allen Xue

(57) ABSTRACT

The present disclosure discloses a dye for industrialization of dyeing cotton fiber in supercritical carbon dioxide that can react with cotton fiber, wherein a preparation method therefor comprises the following steps: dissolving a hydroxyl-containing natural dye in an organic solvent, dropwise adding an alcohol compound containing a halogen group into a reaction system in the presence of an acid-binding agent, precipitating the product with another solvent after the reaction is completed, and then filtrating and drying to obtain the compound described. The obtained compound is used for dyeing cotton fiber in supercritical carbon diox-
(Continued)

ide. The dye provided by the present disclosure is capable of dyeing cotton fiber in supercritical carbon dioxide conditions, and has a better color fastness while dyeing the cotton fiber.

6 Claims, 1 Drawing Sheet

(51) Int. Cl.
*D06P 1/34* (2006.01)
*D06P 3/60* (2006.01)
*C09B 23/10* (2006.01)
*D06P 1/00* (2006.01)

(52) U.S. Cl.
CPC .................. *D06P 1/94* (2013.01); *D06P 3/60* (2013.01); *Y02P 20/544* (2015.11)

(58) Field of Classification Search
CPC ...... D06P 3/60; D06P 1/94; D06P 1/00; Y02P 20/544
See application file for complete search history.

(56) References Cited

FOREIGN PATENT DOCUMENTS

| | | |
|---|---|---|
| CN | 106543765 A | 3/2017 |
| WO | 2013045702 A2 | 4/2013 |

OTHER PUBLICATIONS

Chatchawan, C. et al., "Isoxazole Analogs of Curcuminoids with Highly Potent Multidrug-Resistant Antimycobacterial Activity", European Journal of Medicinal Chemistry, vol. 45, Aug. 5, 2010 (Aug. 5, 2010), 4446-4457.

* cited by examiner

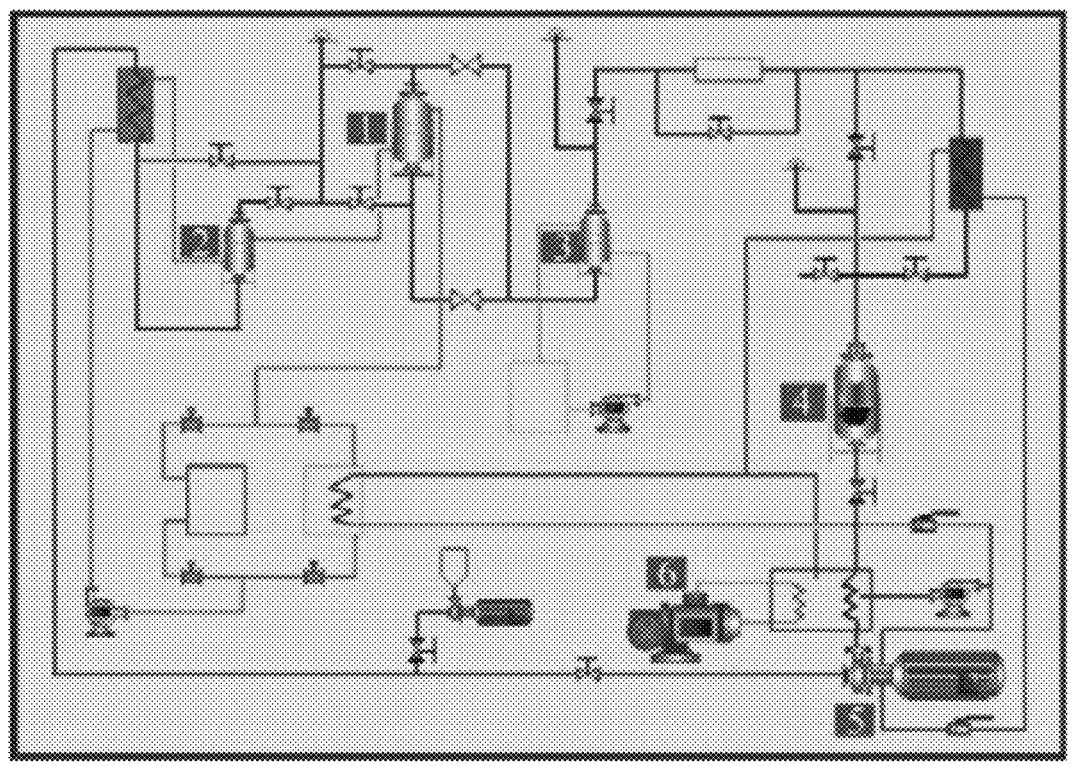

DYE FOR DYEING COTTON FIBER IN SUPERCRITICAL CARBON DIOXIDE, PREPARATION METHOD AND APPLICATION THEREOF

TECHNICAL FIELD

The present disclosure belongs to the field of dyes, and particularly relates to a dye for dyeing cotton fiber in supercritical carbon dioxide that can react with cotton fiber as well as a preparation method and an application thereof.

BACKGROUND ART

The traditional dyeing method of cotton fiber uses water as a medium, and the cotton fiber is dyed by adding a large amount of dye, salt and auxiliaries during the dyeing process. This method not only causes a dilemma of fighting for water between the printing-dyeing industry and the human beings and animals, but also causes serious environmental pollution due to inactivated dye, salt and auxiliaries contained in dyeing wastewater, which restricts the sustainable development of the textile printing and dyeing industry. Supercritical carbon dioxide anhydrous dyeing technology refers to a technology of dyeing fiber in a supercritical carbon dioxide medium, which has the advantages of non-toxic, tastelessness, low recovery cost of dyeing medium, etc., and can solve the wastewater problem in dyeing industry from the source.

At present, the supercritical carbon dioxide dyeing technology has enabled the synthetic fiber to have a satisfactory dyeing effect, and has gradually entered the stage of pilot test and trial production. However, the supercritical carbon dioxide dyeing technology for cotton fiber has not been broken through, which is due to the fact that the dye for cotton fiber contains a mass of sulfonic acid groups, which are hardly soluble in supercritical carbon dioxide. Natural dye has high safety factor, biodegradability, environmental protection and good affinity for natural fiber, and has been applied to dyeing natural fibers such as cotton, linen and silk thousands of years ago. More importantly, the natural dye does not contain the sulfonic acid groups in the structure and has good compatibility with the supercritical carbon dioxide medium.

According to literature reports, many natural dyes, such as turmeric, madder, lithospermum, rhubarb, etc., have certain solubility in supercritical carbon dioxide, have the basic conditions for dyeing cotton fiber in the supercritical carbon dioxide medium. However, the force between natural dye and cotton fiber is weak, and the problems of low color depth and poor color fastness exist after dyeing cotton fiber, which limits the application of the natural dye in the technology for dying cotton fiber in supercritical carbon dioxide.

SUMMARY OF THE INVENTION

In order to overcome the problem of weak force between the natural dye and the cotton fiber in the existing supercritical carbon dioxide dyeing, the present disclosure provides a modified dye that can react with the cotton fiber under a supercritical carbon dioxide condition, which solves the problems of low color depth and poor color fastness after the cotton fiber is dyed with the natural dye.

In order to solve the problems above, the present disclosure provides a hydroxyalkyl-containing natural dye, which has a structure of general formula I:

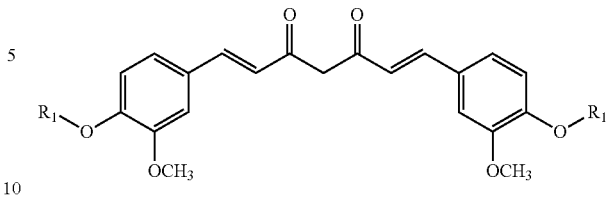

wherein, in the general formula I, $R_1$ is hydroxyalkyl with a structure of $-(CH_2)_n OH$, and n is an integer ranging from 3 to 5.

The present disclosure further provides a preparation method of the dye for dyeing cotton fiber in supercritical carbon dioxide above, which comprises the following steps of:

dissolving a hydroxyl-containing natural dye in an organic solvent A, dropwise adding an alcohol compound containing a halogen group into a reaction system in the presence of an acid-binding agent to perform grafting reaction; and precipitating the product with a solvent B after the reaction is completed, and then filtrating and drying same to obtain the hydroxyalkyl-containing dye for dyeing cotton fiber in supercritical carbon dioxide.

In accordance with an aspect, the alcohol compound containing halogen group has a structure of $X-(CH_2)_k OH$, wherein X is selected from chlorine, bromine or iodine, and k is an integer ranging from 3 to 5.

In accordance with an aspect, the hydroxyl-containing natural dye is curcumin.

In accordance with an aspect, the organic solvent A is N,N-dimethylformamide, dimethyl sulfoxide or acetone.

In accordance with an aspect, the acid-binding agent is potassium carbonate or sodium carbonate.

In accordance with an aspect, the organic solvent B is water.

In accordance with an aspect, the drying is vacuum drying at 50 to 80° C.

In accordance with an aspect, the natural dye is preferably dissolved in the organic solvent A under the condition of 10 to 60° C., and is further preferably under the condition of 35 to 45° C.

In accordance with an aspect, a temperature of the grafting reaction is preferably 50 to 90° C., and is further preferably 75 to 85° C.; and a time of the grafting reaction is preferably 2 to 9 h, and is further preferably 4 to 6 h.

In accordance with an aspect, a molar ratio of the acid-binding agent to the natural dye is 3:1 to 1:5, and is preferably 2:1 to 1:1; a molar ratio of the alcohol compound containing a halogen group to the natural dye is 7:1 to 2:5, and is preferably 5:1 to 4:1.

In accordance with an aspect, a volume ratio of the solvent B to the product of the grafting reaction is 10:1 to 1:1, and is preferably 3:1 to 2:1; and a reaction time for separating out the product from the solvent B is 20 to 90 min, and is preferably 50 to 60 min.

The present disclosure further provides a dyeing method using the dye for dyeing cotton fiber in supercritical carbon dioxide, which comprises the following steps of: crushing the dye into 10 to 100 mesh size in a fineness crusher, placing the crushed dye and cotton fiber into a supercritical carbon dioxide dyeing device, heating the mixture to a temperature of 50 to 150° C., and turning on the high-pressure system to make the pressure of the mixture be 12 to 35 MPa; dyeing for 30 to 150 min under the above condition, then releasing the pressure to 4 to 5 MPa, and recovering the carbon dioxide and the dye at 25 to 40° C.; and releasing the pressure again and cooling the temperature to a normal state to obtain dyed fiber.

In accordance with an aspect, the dye is preferably crushed into 80 to 100 mesh size; the heating temperature of the supercritical carbon dioxide dyeing device is preferably 70 to 150° C., the pressure is preferably 20 to 30 MPa, and the dyeing time is preferably 60 to 120 min.

Fabric color fastness test analysis is performed according to the evaluations of GB/T3921-2008 Textiles—Test for colour fastness—Colour fastness to washing with soap or soap and soda, GB/T7568.2-2008 Textiles—Tests for colour fastness—Standard adjacent fabrics—Part 2: Cotton and viscose and GB/T 12490-2014 Textiles—tests for colour fastness—Colour fastness to domestic and commercial laundering. The results show that the color fastness to rubbing and washing of the dyed fabric can reach grade 3 to 5, both reaching the color fastness standard of water dyed cotton fiber.

Compared with the prior art, the present disclosure has outstanding characteristics of changing the original dyeing manner of cotton fabric, dyeing the cotton fiber through modified natural pigment, and also has advantages of high color depth, high color fastness, clean production, remarkable economic and environmental benefits, etc.

(by volume ratio, a developing solvent to ethyl acetate to petroleum ether is 1 to 3) until no curcumin point appeared in the reactant, which indicates that the grafting reaction was ended.

50 mL water was added into a 100 mL beaker, 22 mL bright yellow reaction solution containing the product was poured into the water under stirring, and the reaction product was fully precipitated in the water under stirring for 1 h. Then, the mixture was filtered, and dried in a vacuum drying oven at 60° C. for 12 h to obtain a product 1, wherein the yield was 55.9%. Spectrogram data of the product 1 was as follows: ES-API (m/z (%)): 255.12 (199) $[M-2H]^{2-}/2$; 1H NMR (400 MHz, DMSO-d6): δ 7.56 (d, J=15.8 Hz, 2H, H-j and H-D, 7.33 (d, J=1.9 Hz, 2H, H-I and H-i'), 7.16 (dd, J=8.1, 1.9 Hz, 2H, H-h and H-h'), 6.84 (d, J=8.1 Hz, 2H, H-g and H-g'), 6.76 (d, J=15.8 Hz, 2H, H-k and H-k'), 6.07 (s, 1H, H-l), 3.85 (s, 6H, H-f and H-f'), 3.83 (obscured signal, 4H, H-b and H-b'), 2.56 (t, J=5.5 Hz, 4H, H-e and H-e'), 2.51 (m, 10H, H-a, H-a', H-c, H-c', H-d and H-d'); IR (KBr): 3231 $cm^{-1}$ (—OH), 2938 $cm^{-1}$ ($v_{C-H}$), 1629 $cm^{-1}$ ($v_{C=O}$), 1588 $cm^{-1}$ ($v_{C=C}$ aromatic ring), 1513 $cm^{-1}$ ($v_{C=C}$ aromatic ring), 1449 $cm^{-1}$ ($\delta_{C-H}$ in-plane deformation), 1291 $cm^{-1}$ ($\delta_{C-H}$ in-plane deformation), 1263 $cm^{-1}$ ($v_{C-O-C}$), 1119 $cm^{-1}$ ($v_{C-O-C}$), 846 $cm^{-1}$ ($\gamma_{=C-H}$ aromatic ring), 805 $cm^{-1}$ ($\gamma_{=C-H}$ aromatic ring), 714 $cm^{-1}$ ($\gamma_{-(CH)4-}$)

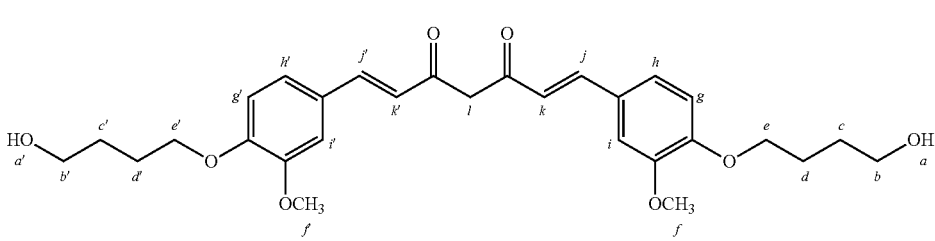

Product 1

BRIEF DESCRIPTION OF THE DRAWINGS

FIG. 1 illustrates a flow chart of supercritical fluid dyeing; wherein, 1—dyeing kettle, 2—dye kettle, 3—separator, 4—circulating pump, 5—high pressure pump, 6—refrigeration machine.

DETAILED DESCRIPTION OF THE PREFERRED EMBODIMENTS

The following embodiments enable those skilled in the art to more comprehensively understand the present disclosure, but the present disclosure is not limited in any way.

Embodiment 1

20 mL N,N-dimethylformamide and 1.09 g curcumin were added into a 50 mL three-necked flask, the three-necked flask was put into a 40° C. constant-temperature water bath, the curcumin was completely dissolved under stirring, and then 1.2 g anhydrous potassium carbonate was added, to make the reaction solution become reddish-brown. Then 2 mL 4-bromobutanol was dropwise added, after the 4-bromobutanol was completely added into the reaction system, the temperature of the constant-temperature water bath was raised to 80° C., and the reaction was continued for 5 h, and the color of the reaction solution gradually turned into bright yellow. Grafting reaction was monitored by TLC Embodiment 2

20 mL N,N-dimethylformamide and 1.09 g curcumin were added into a 50 mL three-necked flask, the three-necked flask was put into a 40° C. constant-temperature water bath, the curcumin was completely dissolved under stirring, and then 2.4 g anhydrous sodium carbonate was added to make the reaction solution become reddish-brown. Then 2 mL 4-bromobutanol was dropwise added, after the 4-bromobutanol was completely added into the reaction system, a temperature of the constant-temperature water bath was raised to 80° C., and the reaction was continued for 5 h.

50 mL water was added into a 100 mL beaker, 22 mL bright yellow reaction solution containing the product was poured into the water under stirring, and the reaction product was fully precipitated in the water under stirring for 1 h. Then, the mixture was filtered and dried in a vacuum drying oven at 60° C. for 12 h to obtain the product 1, wherein the yield was 54.1%.

Application Example 1

1 g product 1 was crushed into 80 mesh size in a fineness crusher and then was placed in a dye kettle of a supercritical carbon dioxide dyeing device (the flow chart was shown in FIG. 1), loose cotton fiber was placed in a dyeing kettle, closed the dyeing kettle, supercritical carbon dioxide was filled in the supercritical dyeing device, the system temperature was increased to 150° C. by heating, opened the high-pressure system to make the pressure be 26 Mpa, then the dye was dissolved and dyeing was performed under this condition for 110 min; then the pressure was reduced to 4-5 MPa, and carbon dioxide and the dye were recovered at 25-40° C.; then the pressure was released again and the temperature was reduced to a normal state; opened the dyeing kettle was to obtain dyed cotton fiber. The dyed cotton fiber was washed with acetone and then washed with water, and the color fastness of the obtained fiber was tested (see Table 1).

Embodiment 3

20 mL N,N-dimethylformamide and 1.09 g curcumin were added into a 50 mL three-necked flask, the three-necked flask was put into a 40° C. constant-temperature water bath, the curcumin was completely dissolved under stirring, and then 1.2 g anhydrous potassium carbonate was added to make the reaction solution become reddish-brown. Then 2 mL 3-bromopropanol was dropwise added; after the 3-bromopropanol was completely added into the reaction system, the temperature of the constant-temperature water bath was raised to 80° C., the reaction was continued for 5 h, and the color of the reaction solution gradually turned into bright yellow.

50 mL water was added into a 100 mL beaker, 22 mL bright yellow reaction solution containing the product was poured into the water under stirring, and the reaction product was fully precipitated in the water under stirring for 1 h. Then, the mixture was filtered, and dried in a vacuum drying oven at 60° C. for 12 h to obtain a product 2, wherein the yield was 61.2%.

Product 2

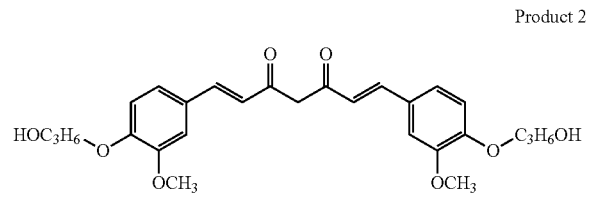

Embodiment 4

20 mL N,N-dimethylformamide and 1.09 g curcumin were are added into a 50 mL three-necked flask, the three-necked flask was put into a 40° C. constant-temperature water bath, the curcumin was completely dissolved under stirring, and then 2.4 g anhydrous sodium carbonate was added to make the reaction solution become reddish-brown. Then 2 mL 3-bromopropanol was dropwise added; after the 3-bromopropanol was completely added into the reaction system, the temperature of the constant-temperature water bath was raised to 80° C., and the reaction was continued for 5 h.

50 mL water was added into a 100 mL beaker, 22 mL bright yellow reaction solution containing the product was poured into the water under stirring, and the reaction product was fully precipitated in the water under stirring for 1 h. Then, the mixture was filtered, and dried in a vacuum drying oven at 60° C. for 12 h to obtain the product 2, wherein the yield was 66.1%.

Application Example 2

1 g product 2 was crushed into 80 mesh size in a fineness crusher and then was placed in a dye kettle of a supercritical carbon dioxide dyeing device (the flow chart was shown in FIG. 1), loose cotton fiber was placed in a dyeing kettle, closed the dyeing kettle, supercritical carbon dioxide was filled in the supercritical dyeing device, the system temperature was increased to 140° C. by heating, opened the high-pressure system to make the system pressure be 25 Mpa, then the dye was dissolved and dyeing was performed under this condition for 120 min; then the pressure was released to 4-5 MPa, and carbon dioxide and the dye were recovered at 25-40° C.; and the pressure was released again, the temperature was reduced to a normal state, and the dyeing kettle was opened to obtain dyed cotton fiber. The dyed cotton fiber was washed with acetone and then washed with water, and the color fastness of the obtained fiber was tested (see Table 1).

Embodiment 5

20 mL N,N-dimethylformamide and 1.09 g curcumin were added into a 50 mL three-necked flask, the three-necked flask was put into a 40° C. constant-temperature water bath, the curcumin was completely dissolved under stirring, and then 1.2 g anhydrous potassium carbonate was added to make the reaction solution become reddish-brown. Then 2 mL 5-bromopentanol was dropwise added; after the 5-bromopentanol was completely added into the reaction system, the temperature of the constant-temperature water bath temperature was raised to 80° C., the reaction was continued for 5 h, and a color of the reaction solution gradually turned into bright yellow.

50 mL water was added into a 100 mL beaker, 22 mL bright yellow reaction solution containing the product was poured into the water under stirring, and the reaction product was fully precipitated in the water under stirring for 1 h. Then, the mixture was filtered, and dried in a vacuum drying oven at 60° C. for 12 h to obtain a product 3, wherein the yield was 43.8%.

Product 3

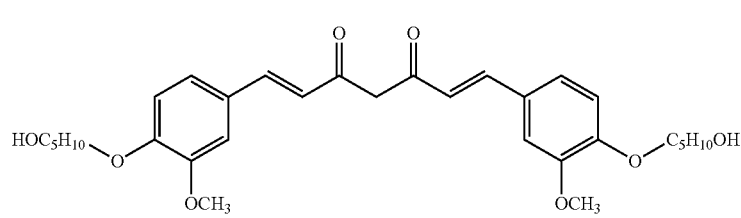

Embodiment 6

20 mL N,N-dimethylformamide and 1.09 g curcumin were added into a 50 mL three-necked bottle, the three-necked bottle was put into a 40° C. constant-temperature water bath, the curcumin was completely dissolved under stirring, and then 2.4 g anhydrous sodium carbonate was added to make the reaction solution become reddish-brown. Then 2 mL 5-bromopentanol was dropwise added; after the 5-bromopentanol was completely added into the reaction system, the temperature of the constant-temperature water bath was raised to 80° C., and the reaction was continued for 5 h.

50 mL water was added into a 100 mL beaker, 22 mL bright yellow reaction solution containing the product was poured into the water under stirring, and the reaction product was fully precipitated in the water under stirring for 1 h. Then, the mixture was filtered, and dried in a vacuum drying oven at 60° C. for 12 h to obtain the product 3, wherein the yield was 39.8%.

Application Example 3

1 g product 3 was crushed into 100 meshes in a fineness crusher and then was placed in a dye kettle of a supercritical carbon dioxide dyeing device (the flow chart was shown in FIG. 1), loose cotton fiber was placed in a dyeing kettle, closed the dyeing kettle, supercritical carbon dioxide was filled in the supercritical dyeing device, the system temperature was increased to 130° C. by heating, opened the high-pressure system to make the pressure of the mixture be 24 Mpa, then the dye was dissolved and dyeing was performed under this condition for 110 min; then the pressure was released to 4-5 MPa, and carbon dioxide and the dye were recovered at 25 40° C.; and the pressure was released again, the temperature was reduced to a normal state, and the dyeing kettle was opened to obtain dyed cotton fiber. The dyed cotton fiber was washed with acetone and then washed with water, and the color fastness of the obtained fiber was tested (see Table 1).

TABLE 1

| Application example | Washing fastness | | | Rubbing fastness | |
|---|---|---|---|---|---|
| | Color change | Cotton staining | Fur staining | Dry | Wet |
| 1 | 4 | 4-5 | 4-5 | 4 | 4 |
| 2 | 4-5 | 5 | 4-5 | 5 | 4-5 |
| 3 | 4 | 4 | 4-5 | 4 | 3-4 |
| Comparison* | 4 | 3 | 4-5 | 4 | 3 |

*Ji Ting, Study on one-step extracting-dyeing technology of Supercritical $CO_2$ of Natural Dye, Thesis of Master's Degree, Dalian Institute of Light Industry, 2007

The invention claimed is:

1. A hydroxyalkyl-containing dye, having a structure according to formula I:

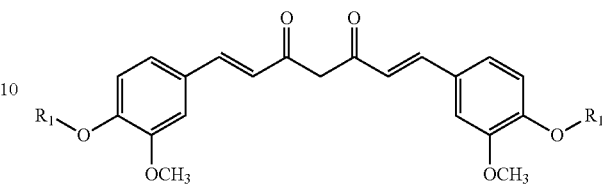

wherein $R_1$ is hydroxyalkyl having a structure of $-(CH_2)_n OH$, and n is 3, 4, or 5.

2. A preparation method of the dye according to claim 1, comprising:
   dissolving a hydroxyl-containing natural dye in an organic solvent to form a solution;
   adding an alcohol compound containing a halogen group and adding an acid-binding agent into the solution;
   precipitating a product from the solution using water; and
   filtrating the product and drying the product to obtain the hydroxyalkyl-containing dye,
   wherein the hydroxyl-containing natural dye is curcumin; and the alcohol compound containing halogen group has a structure of $X-(CH_2)_k OH$, X chlorine, bromine, or iodine, and k is 3, 4, or 5.

3. The preparation method according to claim 2, wherein the organic solvent is N,N-dimethylformamide, dimethyl sulfoxide, or acetone.

4. The preparation method according to claim 2, wherein the acid-binding agent is potassium carbonate or sodium carbonate.

5. The preparation method according to claim 2, wherein the drying is vacuum drying at 50 to 80° C.

6. A dyeing method, comprising
   crushing the dye of claim 1 into 10 to 100 mesh in size;
   adding the crushed dye, cotton fiber, and supercritical carbon dioxide into a supercritical carbon dioxide dyeing device to form a mixture;
   heating the mixture in the dyeing device to a temperature of 50-150° C.;
   increasing a pressure in the dyeing device to 12-35 MPa;
   maintaining the temperature at 50-150° C. and the pressure at 12-35 MPa for 30-150 min;
   reducing the pressure to 4-5 MPa;
   recovering carbon dioxide and the dye from the dyeing device at 25-40° C.; and
   releasing the pressure and cooling the temperature to obtain dyed cotton fiber.

* * * * *